(12) United States Patent
Fitzgerald et al.

(10) Patent No.: US 7,967,808 B2
(45) Date of Patent: Jun. 28, 2011

(54) METHODS, SYSTEMS AND DEVICES FOR ESTABLISING COMMUNICATION BETWEEN HOLLOW ORGANS AND TISSUE LUMENS

(75) Inventors: Peter J. Fitzgerald, Portola Valley, CA (US); Brian K. Courtney, Toronto (CA); Ali Hassan, Mountain View, CA (US)

(73) Assignee: Flea Street Translational, LLC, Menlo Park, CA (US)

( * ) Notice: Subject to any disclaimer, the term of this patent is extended or adjusted under 35 U.S.C. 154(b) by 200 days.

(21) Appl. No.: 11/664,480

(22) PCT Filed: Oct. 6, 2005

(86) PCT No.: PCT/US2005/036047
§ 371 (c)(1),
(2), (4) Date: Mar. 10, 2008

(87) PCT Pub. No.: WO2006/042047
PCT Pub. Date: Apr. 20, 2006

(65) Prior Publication Data
US 2009/0036872 A1    Feb. 5, 2009

Related U.S. Application Data

(60) Provisional application No. 60/616,991, filed on Oct. 7, 2004.

(51) Int. Cl.
*A61M 25/16*    (2006.01)

(52) U.S. Cl. ...................................................... 604/533
(58) Field of Classification Search .............. 604/533, 604/264, 38; 600/585; 606/15; 439/39; 385/57; 206/569
See application file for complete search history.

(56) References Cited

U.S. PATENT DOCUMENTS

| | | | | |
|---|---|---|---|---|
| 3,598,119 A | * | 8/1971 | White | 604/506 |
| 3,808,577 A | * | 4/1974 | Mathauser | 439/39 |
| 3,810,258 A | * | 5/1974 | Mathauser | 439/39 |
| 3,990,447 A | * | 11/1976 | Vega | 604/38 |
| 4,122,947 A | * | 10/1978 | Falla | 206/569 |
| 4,690,495 A | * | 9/1987 | Giannini | 385/57 |
| 4,827,941 A | | 5/1989 | Taylor et al. | |
| 4,875,489 A | | 10/1989 | Messner et al. | |
| 4,969,874 A | * | 11/1990 | Michel et al. | 604/140 |
| 4,997,431 A | * | 3/1991 | Isner et al. | 606/15 |
| 5,334,185 A | * | 8/1994 | Giesy et al. | 604/170.01 |
| 5,607,406 A | * | 3/1997 | Hernandez et al. | 604/264 |
| 5,813,996 A | * | 9/1998 | St. Germain et al. | 600/585 |

\* cited by examiner

*Primary Examiner* — Manuel A Mendez
(74) *Attorney, Agent, or Firm* — Bozicevic, Field & Francis LLP; Bret E. Field; Lynn J. Kidder

(57) ABSTRACT

Methods, systems and devices for establishing communication between organs and/or tissue lumens. The devices include catheters having magnetized distal ends which are configured to magnetically couple to each other such that a coaxial alignment is established between two or more catheters. The systems include two or more the subject catheters. The methods include use of the catheters and magnetically coupling them to establish a continuous passageway between them.

20 Claims, 5 Drawing Sheets

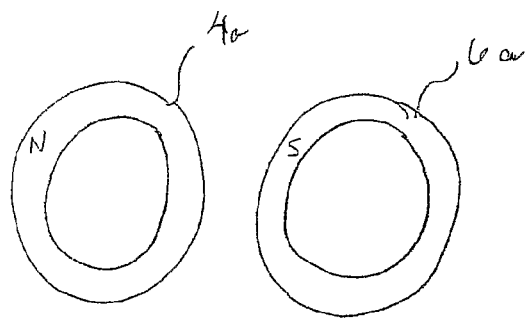
FIG.—5A
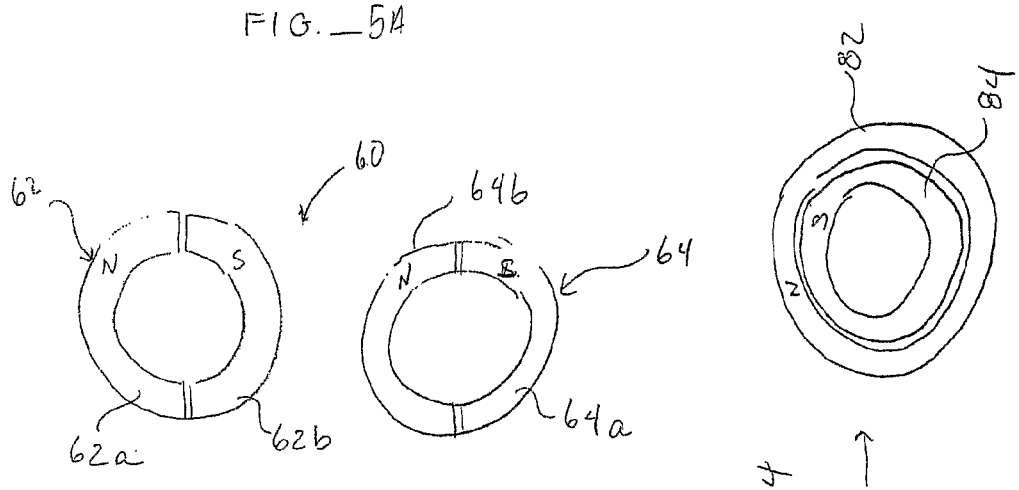
FIG. 5B
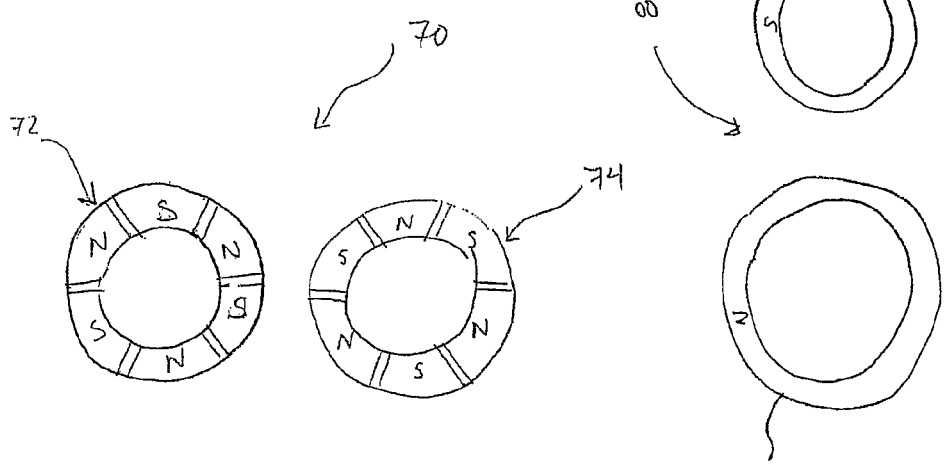
FIG. 5C
FIG. 5D

METHODS, SYSTEMS AND DEVICES FOR ESTABLISING COMMUNICATION BETWEEN HOLLOW ORGANS AND TISSUE LUMENS

BACKGROUND OF THE INVENTION

Catheters have been developed for many treatment and diagnostic applications for various organs (e.g., heart, brain, bladder, etc.) and systems (vascular, alimentary, etc.) of the body. Examples of common catheter-based treatment applications include coronary heart disease (e.g., stent placement, angioplasty, coronary artery bypass, etc.), arrhythmia (e.g., electrophysiology, pacemaker electrode placement, transvenous placement of epicardial leads), cardiac septal defect repair, heart valve repair (e.g. valvuloplasty and percutaneous valve implantation), congestive heart diseases (e.g., providing segmental-myocardial pacing), aneurysms (e.g., placement of vaso-occlusive devices), arteriovenous fistulas (e.g., for dialysis), creation of artificial contacts or shunts between two cardiac chambers as a bridging treatment for certain congenital heart diseases, shunting veins of the portal systems and the inferior cava vein; as well as in intracardiac imaging approaches, which necessitate transseptal navigation of the imaging catheter. As such, catheters serve many functions including, but not limited to, applying energy (e.g., microwave, RF, ultrasound, etc.) to tissue to stimulate nerves, ablating tissue or tightening enlarged orifices, and acting as a conduit for the delivery of implants (e.g., stents, shunts, etc.), instruments (e.g., cutting tools, etc.) other devices (e.g., balloons, filters, etc.) and fluids (e.g., saline, drugs, etc.) to within the body for dilating obstructions or removing growths.

During a catheterization procedure, the physician delivers one or more catheters to a target site within an organ (typically a hollow organ or a chamber within an organ) and/or within a tissue lumen, and attempts to engage a target anatomical structure for one or more of the purposes mentioned above. Catheter delivery often requires navigation through tortuous pathways and passing the catheter through walls of an organ or lumen to access the target site, which target site may be in another organ or lumen or otherwise adjacent the wall being passed through. Often times the passage(s), pathway(s) or hole(s) created to access the target site must be closed upon completion of the procedure due to bleeding or other complications that may occur. Thus, quite frequently, these procedures involve perforating, piercing, cutting, suturing, incising, obliterating, cauterizing, and coagulating tissue, both at a target site and at one or more locations along the delivery pathway of the catheter.

With advancements in endovascular and percutaneous delivery technologies, many more kinds of procedures are able to be performed without invasive or open surgery. One ongoing objective is to reduce the profiles of the delivery catheters and, thus, the procedural instruments as much as possible in order to minimize trauma to the patient and to enable access through very small spaces and vessels. Catheter size (diameter) reduction is particularly challenging in complex procedures that require a variety of different tools (e.g., a cutting instrument and an implant delivery tool) to be delivered to the target site. Even if the size objectives are achieved, it is usually at the sake of procedure time as the number of instruments that can be simultaneously delivered through a catheter is limited. Quite frequently, only one instrument can be delivered and used at a single time.

The venous circulation system, which connects to the right heart, presents a large-caliber, low-pressure conduit system. Some approaches use the venous system to deliver medical devices to the arterial system at the heart level by creating an artificial communication between the two systems.

Virtually all aspects of catheter-based procedures require assisted visualization. Usually, catheterization of hollow organs, especially the heart, is performed under x-ray imaging, e.g., fluoroscopy. Fluoroscopic imaging represents the gold standard for guidance of catheterization procedures because it provides excellent overview on a body-segment and organ level. Although powerful in visualization of dense structures such as bones, prostheses, and other aspects of gross anatomy, fluoroscopy is not as suitable for imaging soft tissue structures, such as muscle and fatty, or fibrous tissues (such as heart valves, various segments of the myocardium, and major afferent or efferent vessels of the heart). Another commonly used modality of medical imaging is ultrasound. Although very effective in visualizing soft tissue, the use of ultrasound in the guidance of catheters has not reached adequate popularity in catheterization laboratories due to technical and logistical limitations.

Without proper visualization, the more likely inaccuracies may occur in the location of tissue augmentation or removal and/or the extent of an intentional disruption or removal of tissue. For example, the location of the actual perforation or penetration site may be mistakenly made a distance from the intended penetration site or, while the location of the penetration or incised site is correct, the size of the hole, cavity or incision created may be larger than is necessary for the particular application.

With the current limitations of visualization technologies and catheter-based instruments, there is still a need for improvement to catheter systems which address the aforementioned shortcomings of the prior art. It would be additionally beneficial if such catheter systems made the endovascular procedures easier, reduced space requirements and minimized procedure time.

SUMMARY OF THE INVENTION

The present invention provides methods, systems and devices for performing medical procedures by establishing communication between organs and/or tissue lumens. The systems include devices, primarily catheters, having magnetized distal ends which are configured to magnetically couple to each other such that a coaxial alignment is established between two or more catheters. The methods include use of the catheters to perform a medical procedure in which the catheters are magnetically coupled within the body to establish a continuous passageway or communication between them. The established passageway may be used to deliver instruments, implants and/or fluids to a target site within the body.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 5A, 5B, 5C and 5D illustrate various exemplary magnet configurations usable with the catheters of the present invention.

DETAILED DESCRIPTION OF THE INVENTION

Figure 1:
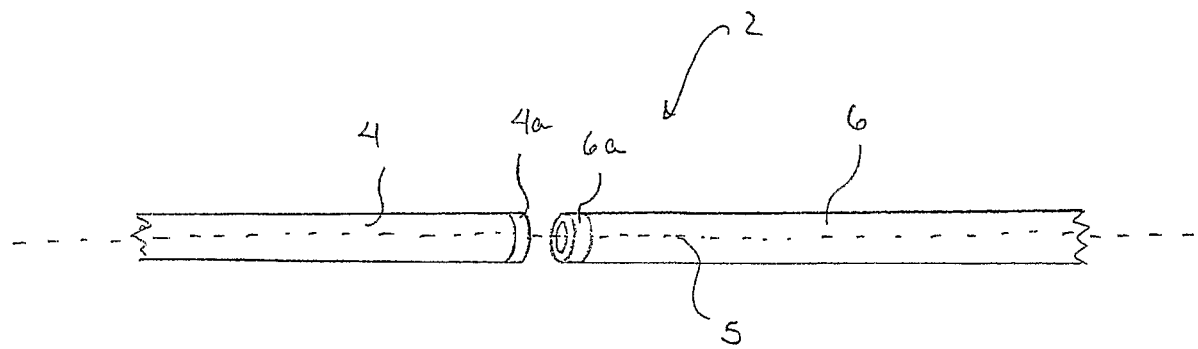
FIG. 1 illustrates an embodiment of a system of the present invention having two distally magnetized catheters, each having a distal magnet positioned substantially perpendicular relative to the longitudinal axis of the catheters.

The present invention provides methods, systems and devices for performing medical procedures by establishing communication between organs and/or tissue lumens. The systems include devices, primarily catheters, having magnetized distal ends which are configured to magnetically couple to each other such that a coaxial alignment is established between two or more catheters. The methods include use of the catheters to perform a medical procedure in which the catheters are magnetically coupled within the body to establish a continuous passageway or communication between them. The established passageway may be used to deliver instruments, implants and/or fluids to a target site within the body.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Generally, the systems of the present invention include at least two devices, such as catheters or elongated tubes, conduits or the like, each having a magnetized distal end. One or more magnets are positioned at the distal end of each catheter and have respective polarities such that a magnetic field is created between the two catheter ends and causes them to be drawn to and coupled with each other in a selected positional relationship. At least a portion of a magnet at each catheter end has a surface on the distal end of the catheter end wherein the catheters are able to align with each other end-to-end whereby a continuous, enclosed conduit or passageway is provided from the proximal end of one catheter to the proximal end of the other catheter. In certain variations, the end-to-end coupling provides a literal "co-axial" relationship between the two catheters where the same longitudinal axis is shared by the catheters. However, in other variations, such an end-to-end coupling need not provide a literal coaxial relationship between the two catheters (e.g., the intersection of the longitudinal axes of the catheters may define an angle) but still provide a continuous, enclosed passageway. Such a continuous, enclosed passageway may also be established by the end-to-end coupling between three or more catheters of the present invention, although not all or none of the catheters literally share a common axis.

The end-to-end coupling of the catheters of the present invention provides certain advantages over prior art catheter systems that are limited to either an end-to-side (perpendicular) coupling between catheters, such as disclosed in International Publication No. WO 97/12555, or a side-to-side (parallel) coupling between catheters, such as disclosed in U.S. Pat. No. 6,669,709. In particular, these prior art catheter systems are not particularly suitable where delivering both catheters into the same confined or narrow space. For example, neither system is suitable where both catheters are to be endovascularly delivered and meet and couple within a single blood vessel. The end-to-side coupling would be practically impossible without damage to the vessel and the side-to-side coupling would be limited to very large vessels.

Referring now to the drawings, there are illustrated various embodiments of the systems of the present invention. FIG. 1 illustrates a system 2 which includes catheters 4 and 5 having magnetized distal ends 4a, 6a respectively. Magnets 4a, 6a are configured as continuous annular rings positioned on at least the forward facing surface of the catheter tips. The magnets may also have surfaces which are exposed on either or both of the exterior and interior sides of the catheters.

Figure 2:
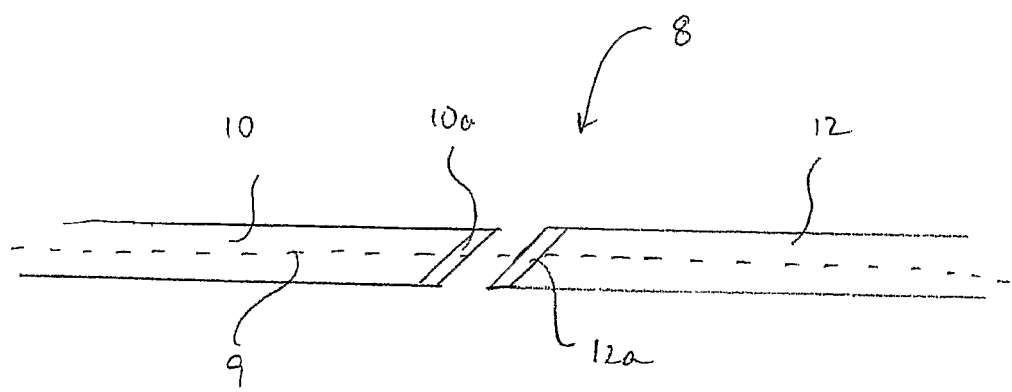
FIG. 2 illustrates another embodiment of a system of the present invention wherein the magnets are positioned at an angle relative to the longitudinal axis of the catheters.

Magnets 4a and 6a are positioned substantially transverse or perpendicular to the longitudinal axis 5 of the respective catheters. However, the positional relationship between the respective magnets and catheters need not be perpendicular but may be at any suitable angle to facilitate the application at hand. For example FIG. 2 illustrates a system having catheters 10 and 12 which have distal end magnets 10a and 12a, respectively, which are positioned at an angle with respect to the catheters' longitudinal axis 9. Where two catheters are employed, the positional relationship between a magnet-catheter pair may be the same for both catheter assemblies, or they may differ from each other. With either configuration, a "coaxial" relationship between catheters is established upon coupling of their magnets whereby a continuous, enclosed conduit or passageway is provided from the proximal end of one catheter to the proximal end of the other catheter.

Figure 3:
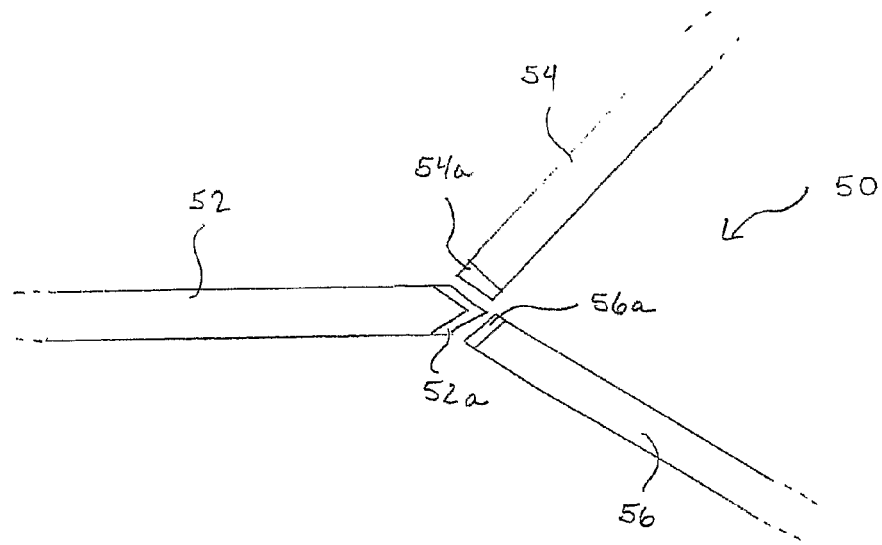
FIG. 3 illustrates another embodiment of a system of the present invention having three catheters having magnetized distal ends which provide a three-way coupling between the catheters.
Figure 4:
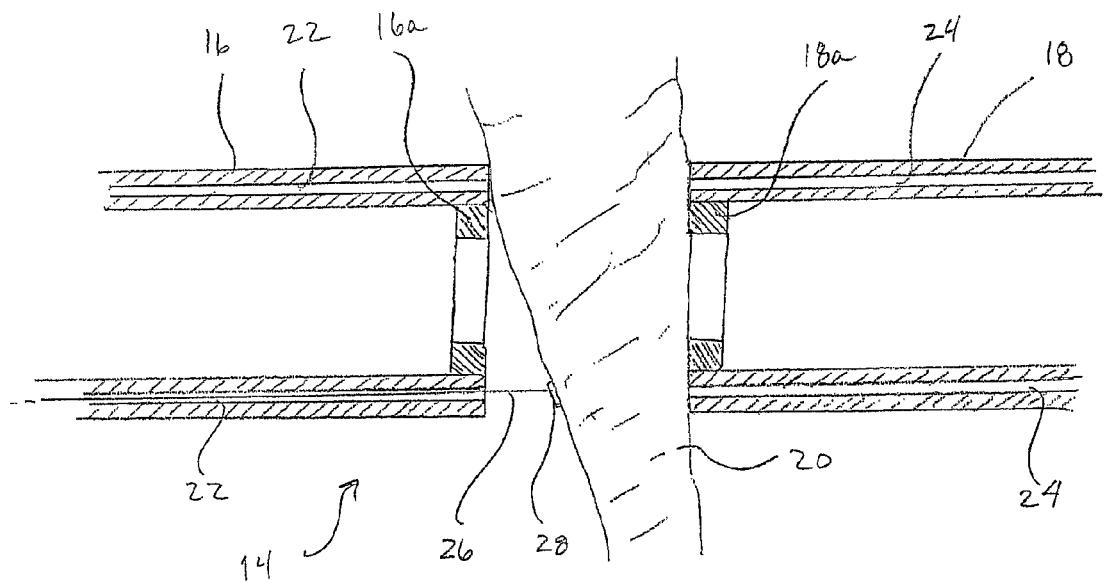
FIG. 4 illustrates another embodiment of a system of the present invention in which the catheters are provided with a distal offset mechanism to facilitate the engagement of tissue.

FIG. 3 illustrates another system 50 of the present invention having three catheters 52, 54 and 56 where catheters 54 and 56 have similar axial juxtapositions with their respective magnetic ends 54a, 56a. Catheter 52 has magnetic end 52a which is bifurcated to allow for lateral coupling with both catheters 54 and 56 to form a "Y" junction between the three. It is appreciated that the number of permutations of possible coupling angles between catheters of the subject systems increases greatly with each additional catheter assembly. The optimal coupling angles between the catheters will largely depend on their respective travel paths and the angle at which they are to be positioned upon reaching the common target site. Certain applications, for example, where two catheters are to couple within a narrow cross-sectional area, e.g., within a vascular lumen, a "head-on" approach may be preferable.

Where the resulting coupling alignment between catheters is unknown or is likely to vary due to, for example, the variation in thickness of tissue captured between their magnetically coupled distal ends, the present invention provides for systems which provide for adjusting the axial orientation of one or both (or more) catheters once engaged against the tissue or the opposing catheter's magnet. One such system 14 is illustrated in FIG. 4 in which two catheters 16, 18 have transverse distal end faces in which annular magnets 16a, 18a, respectively, are coaxially positioned within the respective catheters lumens. An axial adjustment means is provided which includes one or more distally extendable legs or members 26 residing within corresponding channels 22, 24 (where there is a one-to-one ratio, for example, between legs and channels) within the luminal wall of the respective catheters. Each leg 26 may be made of a wire which is pushable at a proximal end so that it can be extended from a port at the distal end of the catheter. Optionally, leg 26 may be provided with a foot 28, which may be configured to pivot, to facilitate engagement with a surface of a tissue structure 20. Leg 26 is selectively extendable to adjust the axial relationship of one catheter 22 with respect to another catheter 24.

The catheter assemblies of FIGS. 1-4 all have magnetic coupling means in the form of a single, continuous annular ring (per catheter); however, the magnetic coupling means of the present invention may include any number of magnets (per catheter) which are discontinuous or interrupted and which may have any suitable shape. With embodiments where a single, continuous magnet is employed, such as magnets 4a and 6a of FIG. 1 which are further illustrated in the planar view of FIG. 5A, the polarities of the two magnets are always opposite, i.e., one magnet has appositive or north pole (N) and the other has a negative or south pole (S). With such a configuration, any relative rotational alignment (i.e., 360°) between the two catheters may be provided and, as such, must be controlled or selected by the physician. Such a configuration is suitable for applications where a lot of flexibility in the alignment of the catheters is necessary. This configuration is also suitable where the particular rotational alignment of the catheters is irrelevant, either with respect to each other or with respect to the target site to which they are delivered, for example, where they are strictly used to transport or deliver an implant, instrument or fluid.

On the other hand, where a very limited number of rotational orientations or only a single rotational orientation between the two catheters or between a catheter and the target site is desired, for example where a mechanism necessary for performing the intended task at the target site is positioned on or deployable from only one side of a catheter (e.g., a port for releasing an embolic member into an aneurysm), the opposing magnets may have a "keyed" arrangement. Two such exemplary magnetic coupling arrangements are illustrated in FIGS. 5B and 5C.

In FIG. 5B, magnetic coupling pair 60 includes a two magnetic means 62 and 64, each comprising a pair of magnets of opposite polarities which form a discontinuous ring. More specifically, semicircular portions 62a and 62b have opposite polarities and semicircular portions 64a and 64b have opposite polarities, where the polarities of 62a and 64a are opposite and those of 62b and 64b are opposite. When operatively aligned, this arrangement ensures that magnetic portion 62a couples with magnetic portion 64a and that magnetic portion 62b couples with magnetic portion 64b. As such, only a single positional relationship is possible between the two catheters.

Another coupling arrangement is provided by magnetic coupling pair 70 of FIG. 5C having magnetic means 72 and magnetic means 74. Each of magnetic means 72 and 74 includes a plurality of discrete magnetic segments where adjacent segments are oppositely polarized. As such, half the segments have a positive polarity (N) and half the segments have a negative polarity (S). Here, each plurality includes three positive segments and three negative segments which arrangement provides a total of three possible rotational alignments between the catheters with which they are employed. The greater the number of magnetic segments, the greater the number of rotational alignments or orientations that can be achieved between coupled catheters.

The magnetic coupling arrangements of the present invention described thus far involve coupling the distally facing surfaces of the opposing magnets or magnetic segments. The present invention also contemplates magnetic coupling arrangements which involve apposition between the exterior surface of the magnetic means of one catheter and the interior surface of the magnetic means of the other catheter. As such, in addition to defining a co-axial relationship with respect to each other, the magnets are concentrically positioned with respect to each other. FIG. 5D illustrates such a configuration where a magnetic coupling means 80 includes magnetic rings 82 and 84 of opposite polarity where the internal diameter of ring 82 and the external diameter of ring 84 are such that ring 84 may be positioned concentrically within ring 82. Any number of magnetic portions or segments may be employed with such laterally-engaging magnetic means to provide a desired keyed relationship between the two catheters. With such embodiments, coupling between the magnets may require direct contact between the magnetic means due to the limited clearance between the two to accommodate a tissue layer or wall.

The magnetic material used with the devices and systems of the present invention is preferably a permanent magnetic, ferromagnetic, ferrimagnetic or electromagnetic material. Suitable magnetic materials include but are not limited to neodymium iron boron (NdFeB), samarium cobalt (SmCo) and alnico (aluminum nickel cobalt).

Alternatively, a current-driven magnet may be used for one or both of the magnetic means.

The amount of force necessary to provide and maintain a coupling between catheters will vary on the application and environment of the location of the target coupling site within the body. For example, where a fluid tight seal is required to be established between the catheters and/or the intracorporeal environment is turbulent or subject to fluid flow pressures (e.g., within a heart chamber), stronger magnets may be required.

In certain embodiments of the subject systems, the magnetic means may be configured to be disengagable from the distal end of the catheter and remain as an implant.

Figure 6A:
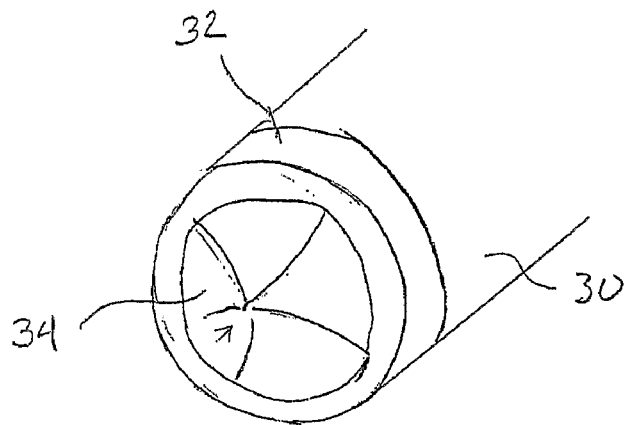
FIGS. 6A, 6B and 6C illustrate various exemplary distal tip configurations of the catheters of the present invention, including a puncturing member, a coring member and a cutting member, respectively.
Figure 6B:
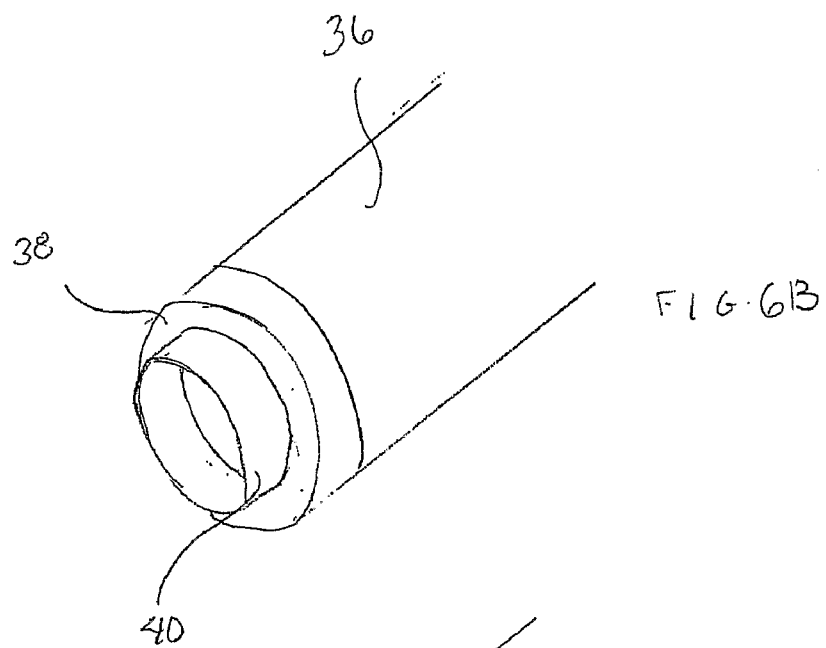
Figure 6C:
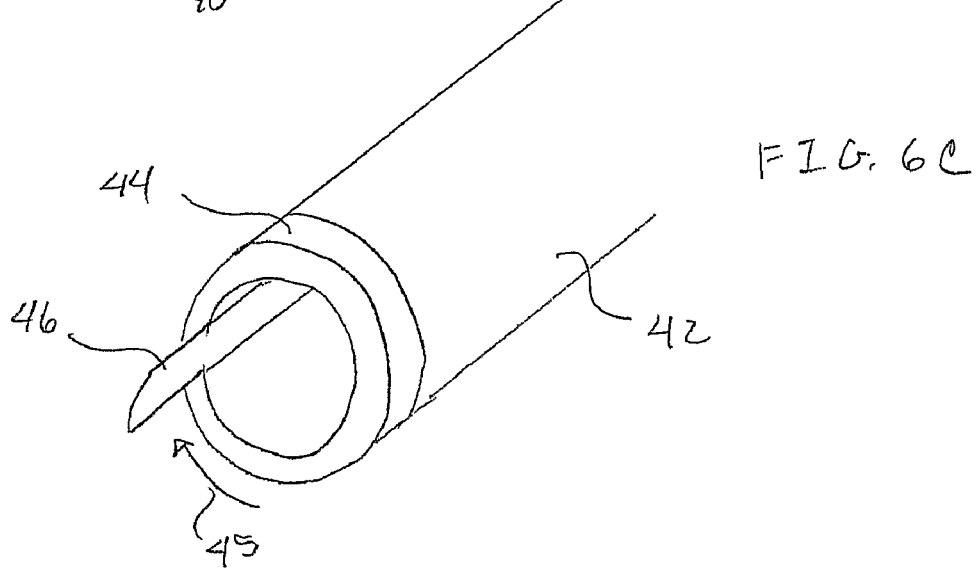

In applications where open communication is to be established between catheters axially separated by tissue structures of contiguous organs or vessels, a perforating object may be required. Such a perforating object may be provided by an instrument separate from but deliverable through one or both the catheter lumens or may be provided by the distal configuration of the catheter tip itself. FIGS. 6A, 6B and 6C illustrate various penetrating means that enable penetration of tissue.

FIG. 6A illustrates a catheter 30 having magnetic means 32 as described above and tissue penetration member 34 positioned within magnetic means 32. Penetration member 34 provides a conical or pointed tip which functions similarly to an obturator. FIG. 6B illustrates another embodiment of tissue penetrating member 40 extending from a magnetized distal end 38 of catheter 36. Penetrating member 40 has an annular wall configuration having a sharp or blade-like distal edge which functions to core tissue. FIG. 6C illustrates a tissue penetrating member 46 in the form of a straight-edged blade extending from magnetized distal end 44 of catheter 42 and which functions to incise tissue. While only several configurations of penetrating members have been illustrated and described, any suitable configuration may be used, including but not limited to a piercing wire, a corkscrew tip, etc.

Where the aforementioned penetrating members are fixed to, integrated with or form the distal end of a catheter, linear translation and/or rotation of the catheter itself causes penetration (e.g., by puncturing, coring or incising, etc.) through the tissue. In other embodiments, the penetrating members are not otherwise fixed to the catheter body and are separately movable there from to penetrate tissue. For example, in some embodiments the penetrating member, e.g., a needle, may be integrated with the magnet itself which is configured to provide pulsatile motion to the needle which functions like a "jackhammer" to puncture tissue.

The penetration members may be used to remove tissue anywhere along the translation pathway of the catheter as well as tissue sandwiched between two catheter ends positioned in adjacent organs, vessels or chambers thereby establishing communication between the two.

The systems of the present invention may be configured, material or physical characteristics and sized for any application and function. For example, catheters of the present invention used for cardiovascular applications will have dimensions and material characteristics similar to conventional cardiovascular catheters. Likewise, catheters of the present invention used for alimentary applications will have dimensions and material characteristics similar to conventional alimentary catheters. Further, the systems may employ mechanisms and functions of conventional catheter systems, including for example, steering mechanisms, visualization markers, etc.

The conduits or catheters of a single system may each have the same configuration and perform the same function. For example, both catheters may be used solely for delivery of one or more other catheters or instruments which are translatable from one delivery catheter to the other delivery catheter. More particularly, when magnetically coupled to each other, either by direct contact between the magnets or with tissue or material captured there between, the catheters may provide a continuous conduit or pathway through which another device (e.g., catheter, guidewire, energy-applicator, cutting instrument, tissue removal instrument, etc.) or fluid (e.g., drug, saline, biologic composition, etc.) may be translated and delivered to a target tissue site or transferred from one catheter to the other. For example, one delivery catheter may be used to "push" an implant or a device to a target site while the other delivery catheter may be used to, "pull" the same implant or device to the target site when pushing is no longer feasible, and visa-versa.

Alternatively, the two or more catheters of the same system may have different configurations and/or functions. For example, one catheter may be configured as a cutting instrument and another corresponding catheter may be configured to receive the cutting end of the cutting instrument after it incises tissue. In other variations, one catheter may be used for guidance (and include a scope and/or lighting means) of one or more other therapeutic catheters.

The systems of the present invention are particularly helpful in situations where it is necessary to penetrate a tissue structure (e.g., vascular, septal or chamber wall) to gain access from one hollow structure to another hollow structure, e.g., from one organ chamber or vessel lumen to another organ chamber or vessel lumen. With conventional catheter systems, even those equipped with videoscopic guidance, a physician attempting to penetrate tissue from one structure to another is left "blind" with respect to the second or receiving structure. This presents the concern of penetrating the tissue structure at the wrong location or at a less than accurate location, or over-penetrating or excessively incising the tissue structure, which may lead to excessive bleeding and require time-consuming and difficult remedial repair. With the present invention, the presence of a second or additional catheter in the secondary or receiving structure which is readily aligned end-to-end with the first or primary catheter mitigates this disadvantage. In other words, the lumen of the secondary catheter is used as a receptacle or receiving space for a cutting member, which itself may be integrated with the primary catheter or a part of a separate a cutting or piercing instrument (e.g., an obturator) delivered through the primary catheter.

Another shortcoming of conventional catheter systems which is addressed by the systems of the present invention is the lack of ability to access a remote target site which requires use of a very long and/or small diameter catheter. The longer and the smaller the catheter, the less steerability and torquability it has. By providing two catheters, where one catheter is delivered from one side or approach to the target site and the other is delivered from another side or approach, in certain applications, the length of each catheter may be substantially less (even as much as half the length) than that of the single conventional catheter. Shorter catheters are easier to steer and navigate. Also, in a system of two-catheters coupled magnetically at the tip, the catheters can be mutually supportive in terms of balancing between steerability/torquability and adaptability to vascular tortuosity. Moreover, the use of two (or more) catheters may provide a physician with more delivery route options which may be more spacious and less tortuous than those routes that may otherwise have to be used when using conventional catheter systems.

Those skilled in the art will appreciate that examples of ideally suited applications of the catheter systems of the present invention include but are not limited to atrial septal defect repair, ventricular septal defect repair, TIPS (i.e., transjugular intrahepatic portosystemic shunt) procedures, in which an artificial tract or shunt in the vascular system is produced, pacing electrode placement, placing laproscopic trocars, create arteriovenous fistulas (for dialysis or anastomosis), forming anastomoses; ligating tissue structures (such as left atrial appendages), delivering biologic material (for angiogenesis or extracellular matrix applications), etc.

Figure 7:
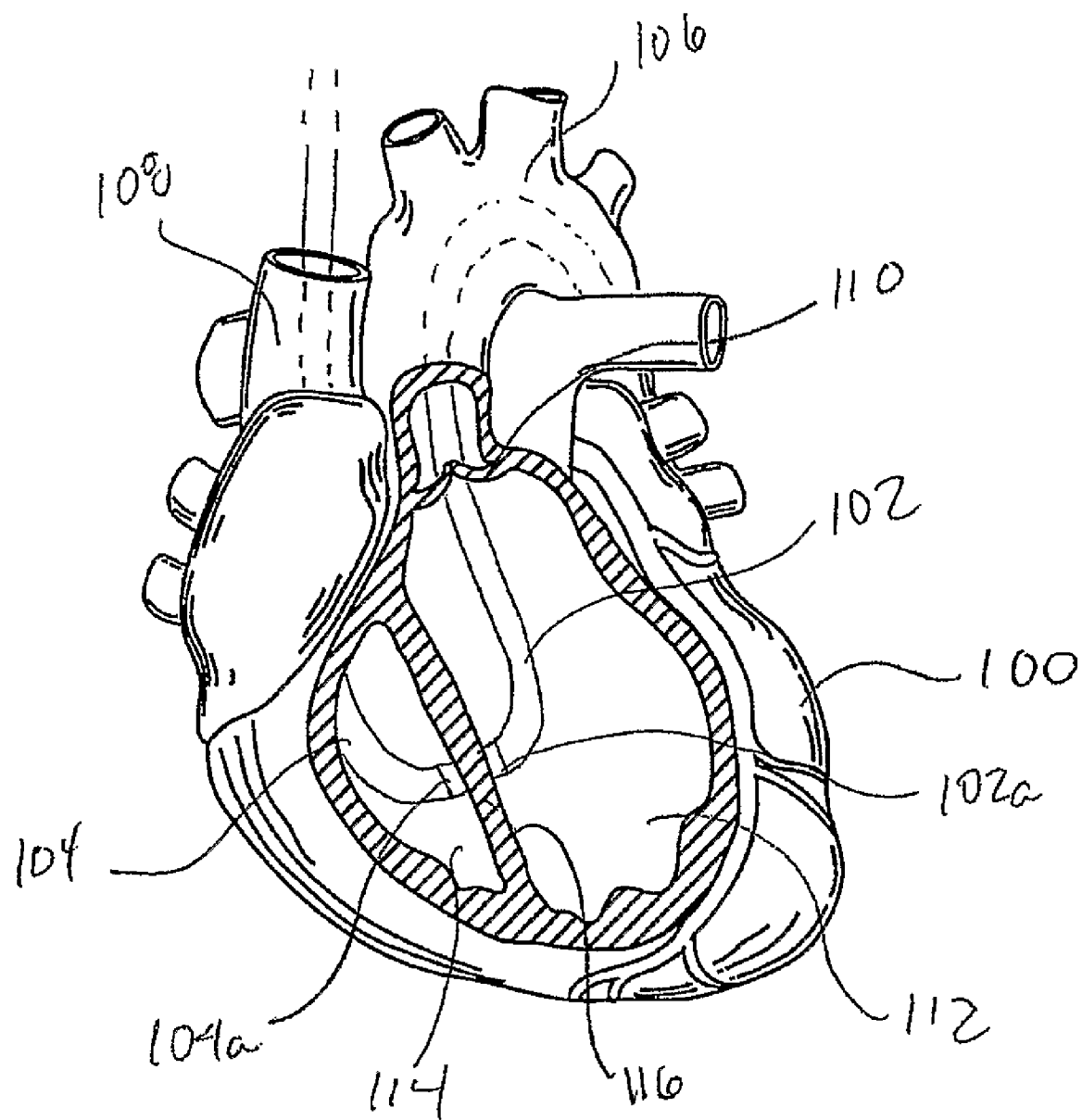
FIG. 7 illustrates use of a system of the present invention to facilitate the exchange of instruments from one anatomical chamber or lumen to another.

FIG. 7 illustrates an exemplary procedure in which a subject system is employed to treat a ventricular septal defect within a heart 100. A first catheter 102 of the present invention is delivered endovascularly through the aorta 106 and across the aortic valve 110 into the left ventricle 112. A second catheter 104 of the present invention is also delivered endovascularly through the superior vena cava 108 to within the right atrium and across the tricuspid valve (not shown) into the right ventricle 114. The catheters are maneuvered and steered to the target site in the septal wall 116. Their respective magnetic means 102a and 104a become magnetically coupled whereby the septal wall 116 is sandwiched there between. As such, a continuous passageway or loop is established through the patient's body. The catheters may then be used to deliver various instruments and other objects or devices known to those skilled in cardiac surgery to repair the septal defect. Delivery, deployment and coupling of the subject devices, as well as steps of the subsequently performed procedure, if necessary, may be performed with or without videoscopic or endoscopic assistance or intra-operative transesophageal echocardiogram (TEE).

The subject devices and systems may be provided in the form of a kit which may include two or more of the above described catheters. The kits may further include catheter-based instruments deliverable through the catheters for performing a medical procedure. Additionally, the kits may include implantable devices, such as sutures, clips, etc., which are also deliverable through the catheters. Instructions for using the various devices and systems may also be provided with the kits.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A system comprising:
   a first percutaneous catheter comprising a magnetized distal end; and
   a second percutaneous catheter comprising a magnetized distal end;
   wherein the magnetized distal ends are configured and have magnetic polarities wherein magnetic coupling between the distal ends provides a coaxial alignment between the catheters.

2. The system of claim 1, wherein each magnetized distal end comprises at least one magnet.

3. The system of claim 1, wherein each magnetized distal end comprises a plurality of magnetic segments wherein adjacent segments are oppositely polarized.

4. The system of claim 3, wherein the plurality of magnetic segments are axially arranged with respect to the longitudinal axis of the catheter lumen.

5. The system of claim 1, wherein the magnetized distal ends are configured whereby the catheters are only able to magnetically couple in a single rotational orientation.

6. The system of claim 1, wherein the magnetized distal ends are configured whereby the catheters are able to magnetically couple in a plurality of rotational orientations.

7. The system of claim 1, wherein at least one of the catheters comprises a tissue-penetrating member.

8. The system of claim 7, wherein at least one of the catheters is configured to receive the tissue-penetrating member.

9. The system of claim 1, further comprising at least one additional catheter having a magnetized distal end.

10. A kit comprising:
    the system of claim 1; and
    Instructions for using the system.

11. The kit of claim 10, further comprising at least one additional catheter having a magnetized distal end.

12. The system of claim 1, wherein the magnetized distal ends are configured to be concentrically positioned with respect to each other when the distal ends are in contact with each other.

13. A method comprising:
    delivering a first percutaneous catheter comprising a magnetized distal end to a target site within a body;
    delivering a second percutaneous catheter comprising a magnetized distal end to the target site; and
    magnetically coupling the distal ends wherein a coaxial alignment is established between the catheters.

14. The medical method of claim 13, further comprising penetrating a tissue structure positioned between the distal ends.

15. The medical method of claim 14, wherein the first catheter is delivered within a first tissue chamber or lumen and the second catheter is delivered within a second tissue chamber or lumen adjacent said first tissue chamber or lumen, and wherein penetrating the tissue comprises establishing communication between the first and second catheters.

16. The method of claim 13, wherein the method further comprises:
    placing the distal end of the first percutaneous catheter on one side of a tissue structure at the target site; and
    placing the distal end of the second percutaneous catheter on the other side of the tissue structure at the target site so that the tissue structure is positioned between the distal ends of the first and second percutaneous catheters.

17. The method of claim 13, wherein the method is a method of ventricular septal defect repair.

18. A device comprising:

a catheter having a distal end comprising a tissue-penetrating member, wherein said distal end is configured for the axial passage of an object and/or fluid there from; and a magnetic element positioned at the distal end wherein the magnetic element comprises at least one magnet having a forward facing surface.

19. The device of claim 18, wherein the magnetic element is configured to be disengagable from the distal end of the catheter.

20. The device of claim 18, wherein the distal end further comprises an axial adjustment means.

* * * * *